United States Patent
Mapiye et al.

(10) Patent No.: US 11,399,807 B2
(45) Date of Patent: Aug. 2, 2022

(54) NON-INVASIVE DETECTION OF INGESTED MEDICATIONS

(71) Applicant: International Business Machines Corporation, Armonk, NY (US)

(72) Inventors: Darlington Shingirirai Mapiye, Randburg (ZA); James Junior Mashiyane, Selcourt (ZA); Gciniwe Dlamini, Johannesburg (ZA); Dineo Andronicah Makoro, Centurion (ZA); Stephanie Julia Muller, Pretoria (ZA); Mpho Mokoatle, Orkney (ZA)

(73) Assignee: International Business Machines Corporation, Armonk, NY (US)

( * ) Notice: Subject to any disclaimer, the term of this patent is extended or adjusted under 35 U.S.C. 154(b) by 365 days.

(21) Appl. No.: 16/674,522

(22) Filed: Nov. 5, 2019

(65) Prior Publication Data
US 2021/0128115 A1    May 6, 2021

(51) Int. Cl.
*A61B 8/00*     (2006.01)
*A61B 8/08*     (2006.01)
(Continued)

(52) U.S. Cl.
CPC .............. *A61B 8/5215* (2013.01); *A61B 5/48* (2013.01); *G06N 3/08* (2013.01); *G06N 20/00* (2019.01);
(Continued)

(58) Field of Classification Search
CPC ........ A61B 8/5215; A61B 5/48; G06N 20/00; G06N 3/08; G06T 7/0016;
(Continued)

(56) References Cited

U.S. PATENT DOCUMENTS 6,663,846 B1 * 12/2003 McCombs ......... A61K 49/0063
424/9.1
6,738,723 B2   5/2004 Hamilton
(Continued)

FOREIGN PATENT DOCUMENTS

EP        1140210 B1    7/2003

OTHER PUBLICATIONS

"Using Smartphones in the Fight Against Tuberculosis", Mar. 13, 2014, Verizon Wireless Archives, 5 pps., <http://www.verizonwireless.com/news/article/2014/03/using-smartphones-fight-against-tuberculosis.html>.

(Continued)

*Primary Examiner* — Khai M Nguyen
(74) *Attorney, Agent, or Firm* — David K. Mattheis; Maeve Carpenter

(57) ABSTRACT

A method for non-invasive detection of ingested medication which provide for one or more processors to receive images of medications designated for a user prior to ingestion of the medications by the user. The one or more processors capture an ultrasound image during ingestion by the user by an ultrasound device removably adhered to a throat area of the user. The one or more processors determine whether contents of the ingestion by the user includes one or more of the medications designated for the user, and responsive to determining the contents of the ingestion by the user includes one or more of the medications designated for the user, the one or more processors generate a confirmation that includes identification of the detected medications ingested by the user.

20 Claims, 4 Drawing Sheets

(51) Int. Cl.
- *A61B 5/00* (2006.01)
- *G06T 7/00* (2017.01)
- *G06N 3/08* (2006.01)
- *G06N 20/00* (2019.01)

(52) U.S. Cl.
CPC .. *G06T 7/0016* (2013.01); *G06T 2207/10132* (2013.01); *G06T 2207/20081* (2013.01); *G06T 2207/20084* (2013.01)

(58) Field of Classification Search
CPC . G06T 2207/10132; G06T 2207/20081; G06T 2207/20084
See application file for complete search history.

(56) References Cited

U.S. PATENT DOCUMENTS

| | | | |
|---|---|---|---|
| 7,366,675 | B1 | 4/2008 | Walker |
| 7,395,841 | B2 | 7/2008 | Geltser |
| 10,398,161 | B2* | 9/2019 | Arne ............... H04B 5/0062 |
| 11,017,892 | B1* | 5/2021 | Knas ............... A61B 5/117 |
| 2005/0038423 | A1* | 2/2005 | Makin ............. A61N 7/02 606/27 |
| 2007/0185615 | A1 | 8/2007 | Bossi |
| 2008/0077430 | A1 | 3/2008 | Singer |
| 2008/0213904 | A1* | 9/2008 | Sliwa ............... A61B 5/117 436/164 |
| 2010/0185456 | A1 | 7/2010 | Kansal |
| 2011/0255762 | A1 | 10/2011 | Deischinger |
| 2012/0065479 | A1 | 3/2012 | Lahiji |
| 2015/0061832 | A1 | 3/2015 | Pavlovic |
| 2016/0132660 | A1* | 5/2016 | Barajas ............ G06Q 10/10 705/2 |
| 2018/0000411 | A1 | 1/2018 | Bhavaraju |
| 2018/0132784 | A1* | 5/2018 | Euliano ............ A61B 5/42 |

OTHER PUBLICATIONS

"Wearable ultrasound patch penetrates the skin to measure blood pressure", Science Highlights, Dec. 14, 2018, U.S. Department of Health & Human Services, NIH, 3 pps., <https://www.nibib.nih.gov/news-events/newsroom/wearable-ultrasound-patch-penetrates-skin-measure-blood-pressure>.

Adee, "App watches you take your pills and knows when you're faking", Technology, Apr. 27, 2016, NewScientist, 4 pps., <https://www.newscientist.com/article/mg23030713-500-app-watches-you-take-your-pills-and-knows-when-youre-faking/>.

Kalantarian, "Non-Invasive Detection of Medication Adherence Using a Digital Smart Necklace", ResearchGate, Conference Paper, Mar. 2015, 7 pps., <https://www.researchgate.net/publication/294111977_Non-invasive_detection_of_medication_adherence_using_a_digital_smart_necklace>.

Olubanjo, "Tracheal Activity Recognition Based on Acoustic Signals", Conf Proc IEEE Eng Med Biol Soc. 2014; 2014: 1436-1439. doi:10.1109/EMBC.2014.6943870, HHS Public Access.

Sonies et al., "Ultrasound Imaging and Swallowing", Normal and Abnormal Swallowing, pp. 119-138, Springer Link, © Springer Science+Business Media New York 2003, Abstract only, <https://link.springer.com/chapter/10.1007/978-0-387-22434-3_8>.

* cited by examiner

NON-INVASIVE DETECTION OF INGESTED MEDICATIONS

FIELD OF THE INVENTION

The present invention relates generally to the field of imagery, and more particularly to ingestion detection by use of ultrasound imagery.

BACKGROUND OF THE INVENTION

Enhancements in computer technology have enabled improvement and advancement in ultrasound imaging to produce results that are exceptionally clear and aren't recognized as being ultrasound images. Improvements in transducer sensitivity, beam formation and image processing speed enable physicians to see detail significantly smaller and deeper in tissue than was previously possible. Development in ultrasound contrast agents provides for greater detail and resolution, and improvements of ultrasound device size has led to hand carried "point-of-care" system, much smaller than their older conventional cart-based systems.

The advancements in ultrasound imaging provides accurate and efficient alternatives for non-invasive imaging of body tissue, organs, and body functions, and the reduction in size of ultrasound devices extends the practical use of ultrasound imaging outside of formal medical treatment facilities.

SUMMARY

Embodiments of the present invention disclose a method, computer program product, and system. The embodiments include a method for non-invasive detection of ingested medication which provide for one or more processors to receive images of medications designated for a user prior to ingestion of the medications by the user. The one or more processors capture an ultrasound image during ingestion by the user by an ultrasound device removably adhered to a throat area of the user. The one or more processors determine whether contents of the ingestion by the user includes one or more of the medications designated for the user, and responsive to determining the contents of the ingestion by the user includes one or more of the medications designated for the user, the one or more processors generate a confirmation that includes identification of the detected medications ingested by the user.

DETAILED DESCRIPTION

Figure 1:
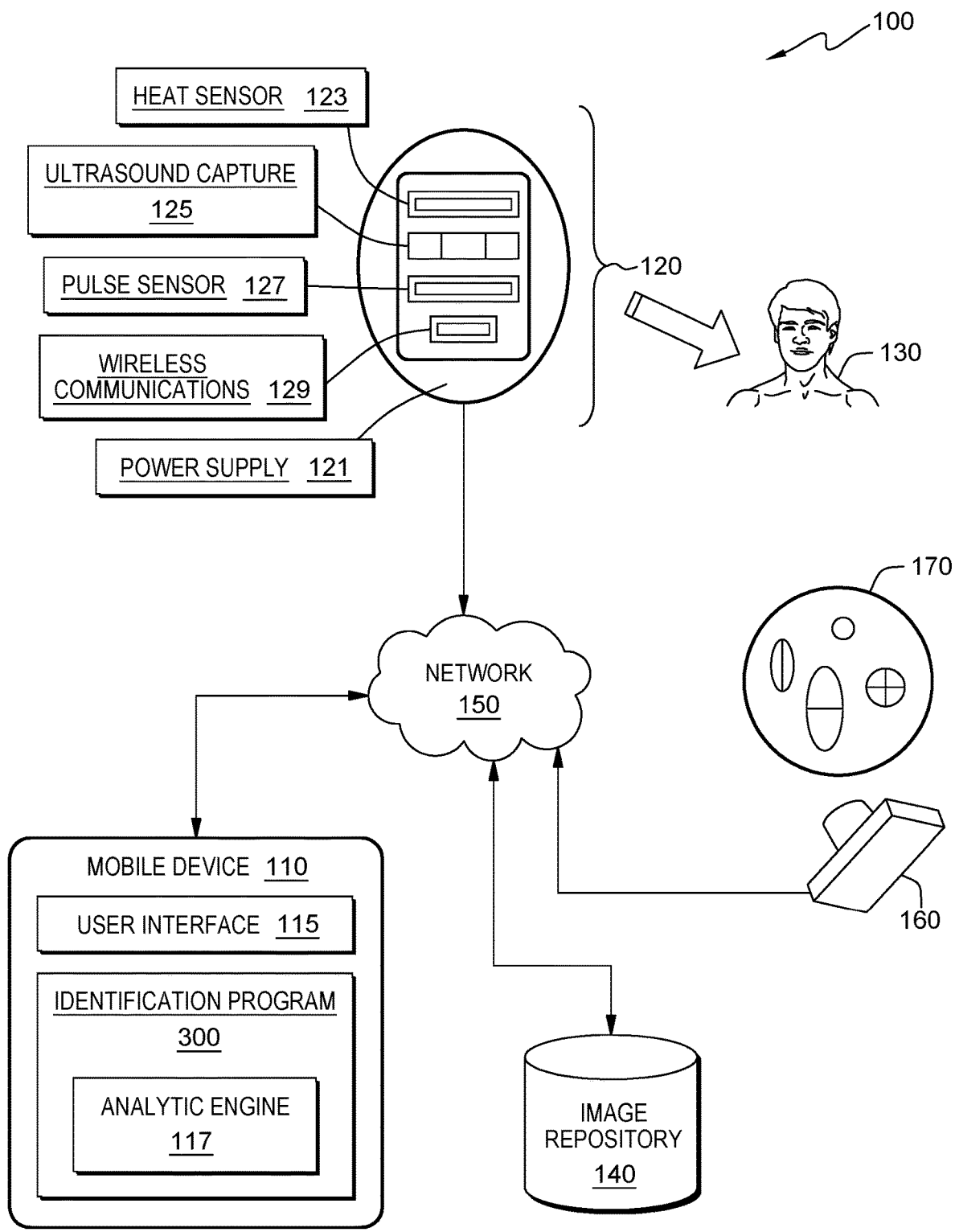
FIG. 1 is a functional block diagram illustrating a distributed data processing environment, in accordance with an embodiment of the present invention.

Embodiments of the present invention recognize that failing to adhere to a prescribed schedule of ingesting medications can result in adverse drug reactions or drug resistance, leading to more serious patient conditions. Non-adherence to medication schedules may result in a loss of control of the treated condition that includes consequences for the patient and may impact others associated with the patient.

Embodiments of the present invention provide a method, system, and computer product for non-invasive identification of ingested medications by use of ultrasound technology to capture images of the ingestion activity. An ultrasound apparatus is activated by sensing body temperature and pulse detection of the patient and is equipped with a connection to a data analytics engine module of a controlling program that analyzes the ultrasound images and determines the shape, size, and count of the ingested medications. The detected medications are classified based on machine learning techniques utilizing previously captured, analyzed, and processed images of medications.

Users of embodiments of the present invention have provided consent to a service in which a non-invasive identification of ingested medications ingested by a user are identified and ingestion confirmed by use of ultrasound technology. In some embodiments, camera images of a user's medications, are identified (labeled), and submitted to an analytical engine for machine learning training. The training enables identification of the medications for a user, prior to ingestion of the medications by the user. The analysis of the images determines size, shape, quantity, and other detectable attributes of the medications, such as markings on the medication surface. In some embodiments the pre-ingestion image captures include a plurality of positions of the medications, offering a three-dimensional view, and in cases where multiple medications may be ingested together, images of combinations of medications are captured. In some embodiments, the output of the analytical engine analysis is stored and is accessible for image recognition processing during subsequent acts of medication ingestion.

In some embodiments, images of captured medication items include ultrasound images and may also include use of membranes mimicking the capture of images by attachment of an ultrasound device positioned on a throat of a user ingesting medications. In some embodiments image analysis of actual medication ingestion instances, or use of similarly characterized placebo look-alikes may be augmented with manual input confirming the identification and attributes of the ingested medication, which may serve as supervised learning of a machine learning technique, further improving and refining the detection capabilities of the analytical engine.

In some embodiments of the present invention, the analytical engine used to analyze captured ultrasound images of ingestion of medications is trained by including images of ingestion of liquids sometimes used when ingesting the medications, such as water, or other ingested liquids. The images capturing the ingestion of the liquids are used to generate a "background" or "baseline" from which ingestion of medications can be more easily discerned. The analytical engine is capable of screening the image contributions from ingested liquids to more precisely perform analysis and identification of the ingested medications.

In some embodiments, captured images are stored in a repository. The captured images include camera and ultrasound images of a user's medications, captured images prior to and during ingestions, ultrasound images taken through membranes approximating skin and tissue of a user's throat area, as well as actual ultrasound images of medication ingestion. The images are analyzed by the analytical engine and processed by modifying the analysis based on captures of background and baseline images. The stored image analysis results are used in convolutional neural networks (CNNs) which are applied to identify the medications included in the images captured during ingestion. In some embodiments the stored image analysis results are maintained in an accessible repository and used in comparison and identification of ingested medications. In other embodiments, the stored image analysis results are stored in a mobile device, communicatively connected to a user-wearable ultrasound device.

If the system is not recording any ingested medication for at least more than three times, a signal is sent to the health care provider for further investigation and another signal is sent to the cloud to investigate if the whole system is working properly.

The present invention will now be described in detail with reference to the Figures. FIG. 1 is a functional block diagram illustrating a distributed data processing environment, generally designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes mobile device 110, ultrasound device 120, user 130, image repository 140, image capture device 160, and medications 170, all connected via network 150.

Network 150 can be, for example, a local area network (LAN), a telecommunications network, a wide area network (WAN), such as the Internet, a virtual local area network (VLAN), or any combination that can include wired, wireless, or optical connections. In general, network 150 can be any combination of connections and protocols that will support communications between mobile device 110, identification program 300, ultrasound device 120, image repository 140, and image capture device 160, in accordance with embodiments of the present invention.

Mobile device 110 is a computing device that includes user interface 115, identification program 300, and analytical engine 117. Mobile device 110 can be a standalone computing device, a smart phone, a tablet computer, a laptop computer, or any other electronic device or computing system capable of receiving, sending, and processing data. In other embodiments, mobile device 110 can represent a computing device interacting with applications and services hosted and operating in a cloud computing environment. In another embodiment, mobile device 110 can be a netbook computer, a desktop computer, a personal digital assistant (PDA), or other programmable electronic device capable of communicating with ultrasound device 120, image capture device 160, image repository 140, and other computing devices (not shown) within distributed data processing environment 100 via network 150. In another embodiment, mobile device 110 represents a computing system utilizing clustered computers and components (e.g., database server computers, application server computers, etc.) that act as a single pool of seamless resources when accessed within distributed data processing environment 100. In some embodiments, mobile device 110 is the computational system performing mobile analytics on captured ultrasound and camera images, and in yet other embodiments, image capture device 160 is an integrated function within mobile device 110. Mobile device 110 provides storage for ultrasound and camera images and in some embodiments, images are sent to external storage (i.e., image repository 140, which may provide cloud storage) for retraining of the models with model instances/rules stored on the mobile device. After retraining, the images on the device may be stored in image repository 140 and are deleted from mobile device 110 to free up storage space. Mobile device 110 may include internal and external hardware components, as depicted and described in FIG. 4.

User interface 115 provides an interface for users to access features and functions of mobile device 110, including identification program 300 and analytical engine 117. In some embodiments of the present invention, user interface 115 provides alert and notification communications regarding a corresponding environment area. In some embodiments, user interface 115 enables connection to and interaction with ultrasound device 120 via identification program 300. In one embodiment, user interface 115 may be a graphical user interface (GUI) or a web user interface (WUI) and can receive user input and display text, documents, web browser windows, user options, application interfaces, and instructions for operation, and include the information (such as graphic, text, and sound) that a program presents to a user and the control sequences the user employs to control the program. In another embodiment, user interface 115 may also be mobile application software that provides an interface to features and functions of mobile device 110. User interface 115 enables a user of mobile device 110 to receive, view/hear, and respond to input, access applications, and perform function available on mobile device 110.

Identification program 300 receives ultrasound images captured by ultrasound capture 125, transmitted by wireless communications 129 of ultrasound device 120 and provides non-invasive identification of medications during a user ingestion activity. Identification program 300 works in conjunction with analytic engine 117 and image repository 140 to identify medications ingested by a user. In some embodiments of the present invention, analytic engine 117 operates as a component module of identification program 300. Identification program 300 includes machine learning training of analytic engine 117 for identification of ingested medications by a user, based on imagery of the medications, ingestion of the medications and baseline images of only liquid ingested that may accompany medication ingestion. In some embodiments, training image captures may include camera images of medications in various placements, arrangements, angles, combinations and overlap. Training image captures may also include ultrasound images labeled with the known medication ingested by a user or may include ultrasound images of medications taken through membranes intended to approximate skin and tissue of a user's throat area.

In some embodiments, identification program 300 stores the analyzed images from analytic engine 117 in a repository, such as image repository 140, for access and use in identification of ingested medications of a user. Identification program 300 receives one or more ultrasound images captured during ingestion of medications by a user. Identification program 300 receives the captured images and sends the images to analytic engine 117. Identification program 300 receives the processed images from analytic engine 117 and determines the identification of medications detected in the processed images by accessing labeled images from image repository 140. Identification program 300 confirms identification of medications based on the comparison of the known medication images that are processed by analytic engine 117 and stored in image repository 140 and the processed results of the ultrasound images captured during user ingestion of the medications. Identification program 300 stores ultrasound images for a designated period of time, and not used or previously used by the analytic engine 117 for training identification program 300 deletes the images.

Analytic engine 117 is depicted as an imagery analysis module of identification program 300. In some embodiments of the present invention, analytic engine 117 operates with identification program 300 on the same host device, for example, mobile device 110 as depicted in FIG. 1. In other embodiments, analytic engine 117 may operate on a remote computing device (not shown) communicatively connected with identification program 300 via network 150. In some embodiments, analytic engine 117 includes a convolutional neural network (CNN or similar variant) for analyzing captured imagery, in other embodiments, analytic engine 117 is a shift invariant or space invariant artificial neural network (SIANN). In some embodiments, analytic engine 117 is trained by supervised learning techniques of image analysis, using labeled images of medications in various spatial arrangement and combinations, ingestion of liquids, and ingestion of medications and liquids, and in some embodiments, analytic engine 117 is further trained by unsupervised learning techniques.

Ultrasound device 120 is an attachable device for capturing ultrasound images of ingestion of medications by a user. In some embodiments of the present invention, ultrasound device 120 is temporarily attached to the throat area of a user, below the ear, and remains in contact with the user during ingestion, and can be subsequently removed. In other embodiments, ultrasound device 120 is a wearable device that may be attached to the throat area of a user and worn for a designated period of time and is removable as necessary or appropriate. Ultrasound device 120 includes heat sensor 123, ultrasound capture 125, pulse sensor 127, wireless communications 129 and power supply 121. In some embodiments ultrasound device 120 includes ultrasound gel (not shown), as a component of attachment to a user to improve imagery results.

Heat sensor 123 and pulse sensor 127 provide biometric input, which is used to initiate function of ultrasound device 120 when temporarily worn. In some embodiments, power to ultrasound 120 is saved by a "sleep" or off state, and detection of a common skin temperature and pulse rate range provides a wake-up function for ultrasound device 120. In other embodiments, detection of a normal skin temperature by heat sensor 123 and/or a normal pulse range by pulse sensor 127 transitions ultrasound 120 from a sleep or off state to a ready state and indicates the state on user interface 115 of mobile device 110. From mobile device 110 the initiation of image capture may be initiated from the ready state notice on user interface 115.

Ultrasound capture 125 is a component of ultrasound device 120 that includes generation, transmission, and receipt of ultrasound signals capturing an image. In some embodiments of the present invention, ultrasound capture 125 is activated by sensing body temperature and/or pulse detection of the patient and initiates capture of images. In other embodiments, the detection of body skin temperature and/or pulse detection of the user activates ultrasound capture 125 to a ready state, and image capture begins subsequent to input from user interface 115 of mobile device 110. Ultrasound capture 125 transmits captured images via wireless communications 129 to identification program 300 and sent to analytic engine 117 for imagery analysis, and ultrasound capture 125 is powered by power supply 121.

Wireless communications 129 is a component of ultrasound device 120 and enables transmission of captured ultrasound images to identification program 300, operating on mobile device 110, and ultimately sent to analytic engine 117 for analysis. In some embodiments, wireless communications 129 establishes a Wi-Fi connection to network 150, a wireless cellular connection (i.e., 3G, 4G, 5G), in other embodiments, the connection may be made via Bluetooth, radio frequency, or other wireless connection technology Power supply 121 provides a source of power to the components of ultrasound 120, enabling the detection of heat sensor 123, the detection of a pulse rate of pulse sensor 127, the generation and receipt of ultrasonic signals from ultrasound capture 125, and the transmission of captured ultrasound images from ultrasound capture 125 to identification program 300 via wireless communications 129 and network 150. In some embodiments, power supply 121 includes a rechargeable battery as a power source, and in other embodiments power supply 121 is recharged wirelessly.

User 130 is depicted in FIG. 1 as an image of a user. User 130 has provided consent opting-in for use of ultrasonic device 120, mobile device 110, image repository 140, image capture device 160, and medications 170, working collectively to identify and confirm ingestion of medications. User 130 registers with the system, using user interface 115 of mobile device 110, providing consent. User 130 receives ultrasound device 120 as an attachment patch or a wearable device, placed on User 130's throat, below the ear. Previously, camera images of medications 170, taken by capture device 160 are analyzed by analytic engine 117 and stored in image repository 140. Images of medications 170 are used to train analytic engine 117 and identification program 300 to identify ingested medications. In some embodiments user 130 ingests one or more medications, which may be ingested one at a time for multiple medications or may be ingested in combinations for multiple medications. Ultrasonic device 120 captures images of the ingested medications which are analyzed to determine identification of the ingested medications.

Image repository 140 is a storage location for imagery analysis results. In some embodiments, image repository 140 is located and operates on mobile device 110. In other embodiments, image repository 140 is located external to mobile device 110 and is communicatively connected to mobile device 110 and accessible to identification program 300 and analytic engine 117. In some embodiments, image repository 140 includes the processing results from analytic engine 117 of camera captured images of medications, ultrasound images of ingested medications, ultrasound images of ingested liquids, and modification of ultrasound ingested medications based on the baseline results of ingested liquids. In some embodiments, image repository 140 includes ultrasound images captured through a membrane approximating the skin and tissue of a user's throat area. In some embodiments, the image analysis results stored in image repository 140 are labeled to identify the particular ingested medication associated with the image and used for machine learning and neural network training of analytic engine 117.

Image capture device 160 is an image capturing device for generating images of medications 170. In some embodiments, image capturing device 160 is a camera generating digital images of medications 170. In other embodiments, image capturing device 160 is capable of capturing digital images providing a 3-dimensional view and used for various combinations and spatial arrangements of medications, including overlapping of medications. In some embodiments, image capture device 160 is an integrated component of mobile device 110.

Medications 170 represents medications, typically pills, that are designated for a user. Each item of medications 170 includes attributes contributing to identification of the particular medications, such as shape, size, and markings.

Figure 2:
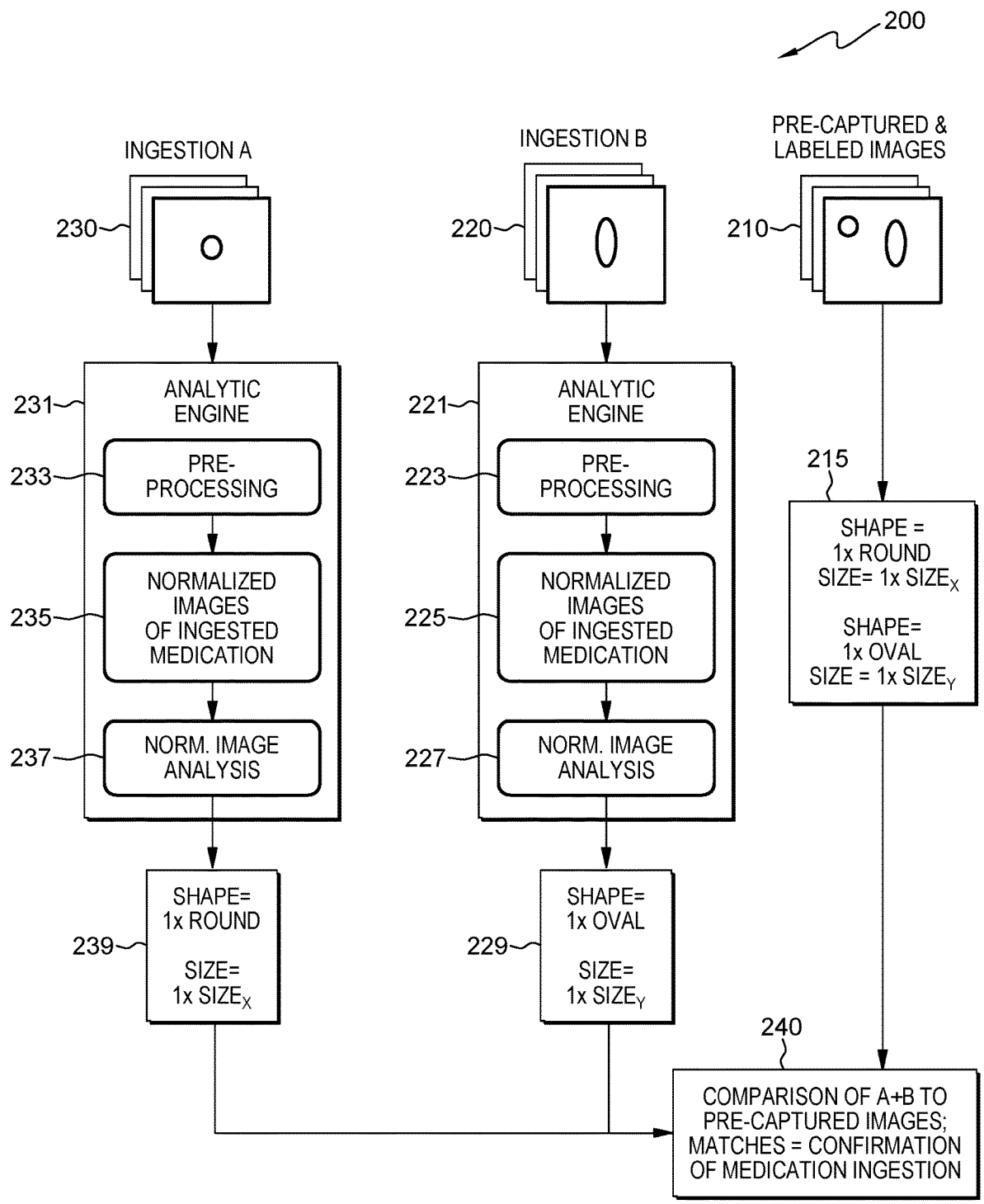
FIG. 2 illustrates implementation paths of a multi-step ingestion example, in accordance with an embodiment of the present invention.

FIG. 2 illustrates implementation paths of a multi-step ingestion example, in accordance with an embodiment of the present invention. FIG. 2 includes ingestion A path, ingestion B path, and pre-captured and labeled images path. FIG. 2 illustrates processing of ingestion images of multiple step ingestion of medications, for example one medication is ingested by a user, followed by another ingestion of a second medication by the same user. In ingestion A path, ultrasound device 120 captures and transmits ingestion images 230, which identification program 300 (FIG. 1) receives and sends to analytic engine 231. Ingestion images 230 are depicted as images of a small round medication captured from a first ingestion of the user. Analytic engine 231 performs pre-processing 233 on ingestion images 230. Pre-processing 233 involves modifying ingestion images 230 to remove baseline image contributions from liquids ingested with medications and other baseline artifacts of captured images to more accurately detect and identify ingested mediation from ingestion images 230. Pre-processing of ingestions images 230 results in normalized images 235.

Analytic engine 231 performs normalized image analysis 237 on normalized images 235 of ingestion images 230, which produces a result with characteristics of the ingested medication. Normalized analysis 237 involves detecting the edges, contrasts, and features of normalized images 235, resulting in an output that determines shape, size and other determined markings or characteristics of the ingested medication, as depicted by image analysis output 239 which includes a determination of one round-shaped item of size (x).

FIG. 2 also includes ingestion B path illustrating a second ingestion of medications by the same user of ingestion A path. Ingestion B path includes ingestion images 220, which ultrasound device 120 captures and transmits to identification program 300 (FIG. 1). In addition, identification program 300 sends ingestion images 220 to analytic engine 221. Analytic engine 221 is depicted as a separate analytic engine for clarity and convenience of describing the multiple-ingestion paths. Embodiments of the present invention perform both ingestion A path and ingestion B path involving the same analytic engine (i.e., one of analytic engine 231 or analytic engine 221), with one ingestion event following the other. Ingestion images 220 are depicted as images of a single large, oval-shaped medication captured from a second ingestion of the user. Analytic engine 221 performs pre-processing 223 on ingestion images 220. Pre-processing 223 involves modifying ingestion images 220 to remove baseline image contributions from liquids ingested with medications and other baseline artifacts of captured images to more accurately detect and identify ingested mediation from ingestion images 220. Pre-processing of ingestions images 220 results in normalized images 225.

Analytic engine 221 performs normalized image analysis 227 on normalized images 225, of ingestion images 220, which produces a result with characteristics of the ingested medication. Normalized analysis 227 involves detecting the edges, contrasts, and features of normalized images 225, resulting in an output that determines shape, size and other determined markings or characteristics of the ingested medication, as depicted by image analysis output 229 which includes a determination of one oval-shaped item of size (y).

FIG. 2 includes pre-captured and labeled images path that includes pre-captured images 210, which are collection of images previously captured and modified to remove baseline image contributions, and includes identification of shape, size and other characteristics of respective medications. In some embodiments, pre-captured images 210 includes images of individual medications and images of combinations of medications in various positions and arrangements and includes instances of overlap of medications. Pre-captured images 210 includes images 215 which identify a round-shaped medication of size (x) and an oval-shaped medication of size (y).

Ingestion A path, ingestion B path and pre-captured and labeled images path converge at comparison 240. The output of ingestion A path and ingestion B path are combined to consider two separate ingestion events of a multi-step ingestion in which a first ingestion is followed by a second ingestion of medications by the same user. In comparison 240, image analysis output 239 and image analysis output 229 are compared to images 215. Identification program 300 can determine a match between image analysis output 239 and image analysis 229 with images 215 to be considered confirmation of identification of medications ingested.

In some embodiments, if a match is not determined between pre-captured and labeled images 210 and image analysis outputs 239 and 229, which fails to identify ingested medications, or indicates an absence of medications, identification program 300 generates an notice or alert displayed on user interface 115 of mobile device 110 (FIG. 1). In other embodiments, a notification may be transmitted to other smart devices or computing devices (not shown).

Figure 3:
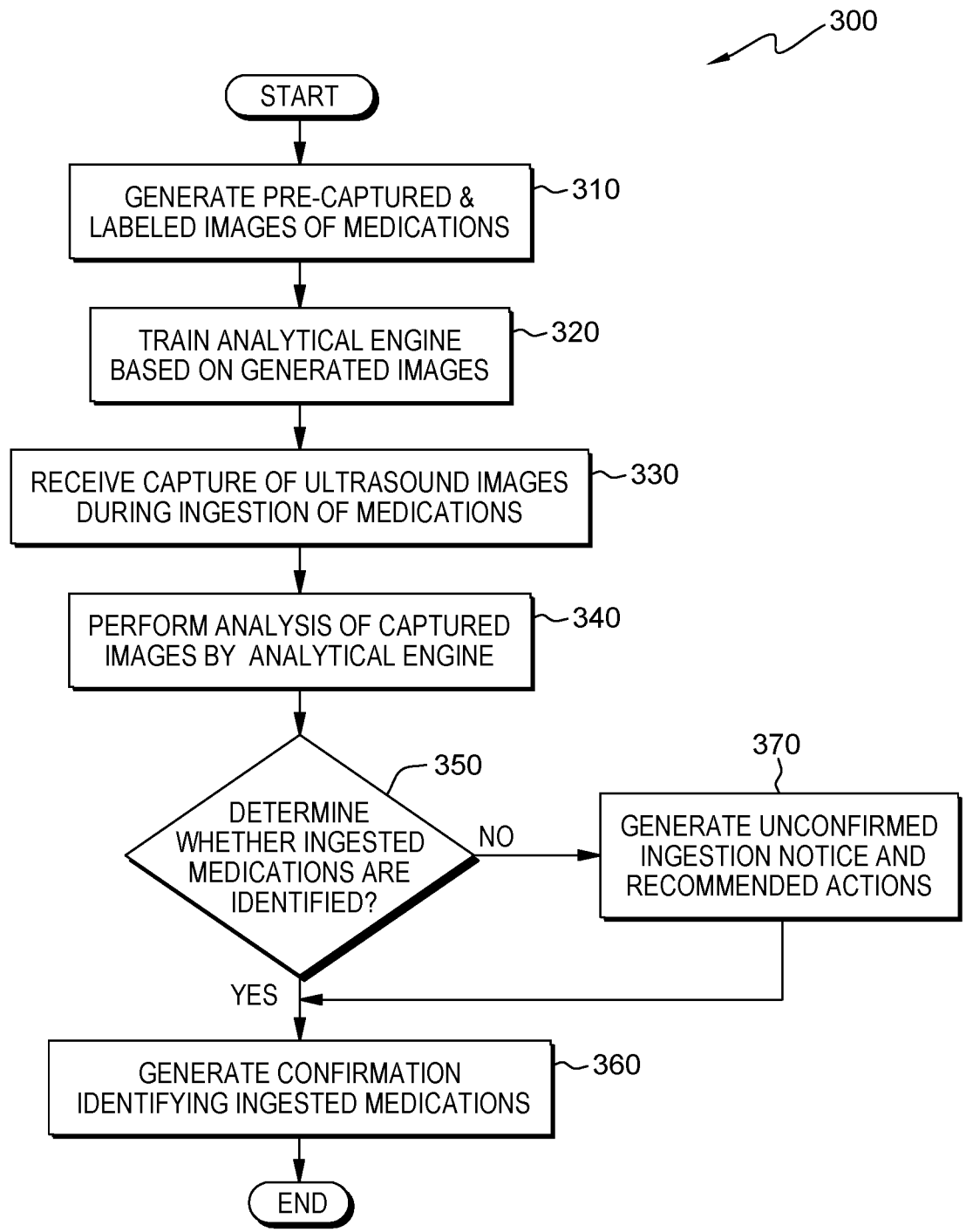
FIG. 3 is a flowchart illustrating the operational steps of an identification program operating within the distributed data processing environment of FIG. 1, in accordance with an embodiment of the present invention.

FIG. 3 is a flowchart illustrating the operational steps of identification program 300 that includes functions of analytic engine 117 operating within distributed data processing environment 100 of FIG. 1, in accordance with an embodiment of the present invention. Identification program 300 generates pre-captured and labeled images of medications (step 310). In an example embodiment, identification program 300 receives medication images generated by ultrasound capture 125 of ultrasound device 120. Identification program 300 can utilize analytic engine 117 to process and label the medication images with the identification of the medication, along with data associated with the size, shape and other characteristics of the medications. In some embodiments, camera images of medications are included in the pre-capture and labeling of medication images.

In an example embodiment where identification program 300 monitors and confirms ingestions of multiple medications, the pre-captured and labeled images of medications include combinations of the medications in various arrangements and may include images of overlap of medications. In some embodiments, pre-captured and labeled images of medications include images of medications captured through a membrane to simulate the skin and tissue of a user's throat. The generation of pre-captured and labeled images of medications includes modification of images in which baseline attributes are removed from the ingestion of medication images to more clearly render image details of the medications. Labeling of images includes identification of the medication, the size, shape, and other distinguishing characteristics, such as imprints of numerals or text and other markings. In some embodiments, a machine learning model is trained external to mobile device 110 and deployed on the user's mobile device. Analytic engine 117 operating on mobile device 110 pre-process the incoming ultrasound image, loads the image to the trained model and generates results. For further training, images captured by the user can be sent to the machine learning model for retraining, then a new and updated model is again deployed on mobile device 110, continually improving results.

Identification program 300 trains analytical engine 117 based on the generated pre-captured and labeled images of medications (step 320). Identification program 300 includes operations to train analytical engine 117 for performing analysis of ultrasound images of ingested medication. In some embodiments of the present invention, training of analytic engine 117 includes use of deep neural networks, such as a convolution neural network that includes an input and output layer, as well as one or more hidden layers. The training includes use of labeled images of medications and ingested medications and involves adjustments to weights associated with connections from layers to optimize outputs to align with the known labels of images. In some embodiments, other machine learning techniques employing supervised learning, may be used to train analytic engine 117.

For example, camera images of medications 170 are captured from image capture device 160, and ingested images of previously identified medications are captured by ultrasound capture 125 of ultrasound device 120 transmitting the images to identification program 300 by wireless communications 129, via network 150. The received images may also include ingestion of liquids commonly included with ingestion of medications, such as water. The images, the labeling identifying the images and attributes of the images are input to a neural network of analytic engine 117. The weights of each input and connection to layers of the neural network are modified as the network progresses forward and backward to optimize inputs resulting in outputs, and outputs processed back to inputs.

Identification program 300 receives a capture of ultrasound images during ingestion of medications (step 330). Identification program 300 receives one or more ultrasound images from ultrasound device 120 during ingestion of medications by a user. Ultrasound device is attached to the user, for example, on the user's throat below the ear. The images of ingested medication are captured by ultrasound capture 125 and transmitted to identification program 300 by wireless communications 129 via network 150.

Identification program 300 provides the received images as inputs to analytic engine 117, which is a module of identification program 300. Identification program 300 utilizes analytic engine 117 and performs analysis of the captured images (step 340). In some embodiments of the present invention, identification program 300 performs a pre-processing step in which baseline ultrasound images are used to modify captured ultrasound images of ingested mediations to remove the baseline attributes and more clearly render the data associated with the ingestions of the medications. In some embodiments, analytic engine 117, as a module of identification program 300, performs imagery analysis of the received ultrasound images captured during ingestion of medications, and determines edges, shapes, sizes, and characteristics of medications within the ultrasound images.

Identification program 300 determines whether the ingested medications are identified (decision step 350). Identification program 300, in conjunction with analytic engine 117, performs a comparison of analytical imagery data of pre-captured images of medications, pre-processed to remove baseline attributes from the imagery data, to the pre-processed images captured during ingestion of medications by the user. Identification program 300 compares size, shape, and characteristics of the images to determine whether there is a match. For example, identification program 300 provides the images of user ingestion to analytic engine 117, a module of identification program 300.

Analytic engine 117 receives and pre-processes images of user ingestion, in which baseline ultrasound attributes of the ingestions, such as liquid accompanying ingestion of medications as well as attributes from skin and tissue of the user, are identified and used to modify the image data for more accurate and clear identification of ingested medications. Analytic engine 117 accesses image repository 140 and retrieves pre-captured image data of medications, which includes images of ingested medications, simulated ingestion of medication, and camera images of medications, which have been pre-processed to modify the image data with respect to baseline attributes. Analytic engine 117 compares the pre-captured image data and the image data of the user's ingestion and determines if medications are detected and match pre-captured medication images.

For the case in which identification program 300 determines that the images captured during user ingestion does not match the pre-captured images (step 350, "NO" branch), identification program 300 generates an unconfirmed ingestion notice and provides recommended actions (step 370). Comparing the pre-captured images from image repository 140 to the images captured from user ingestion, identification program 300 determines that there is not match in comparison of images and generates an "unconfirmed ingestion of medications" notice. In some embodiments, the notice may indicate that an ingestion event occurred, but no medications were detected, or in other embodiments, the notice may indicate that medications were detected but were unidentified. In yet other embodiments, the notice may indicate that no ingestion event was detected. In some embodiments, the notice may be a notification sent to a pre-determined messaging device, such as user interface 115 of mobile device 110. In other embodiments, the notice may include recommended actions to be taken to further determine the status of medications expected during the user ingestion.

For the case in which identification program 300 determines that the images captured during user ingestion do match pre-captured images of medications (step 350 "YES" branch), identification program 300 generates a confirmation identifying the ingested medications (step 360). Comparing the pre-captured images from image repository 140 to the images captured from user ingestion, identification program 300 determines that there is a match in comparison of images and generates a message confirming the identification of ingested medications. In some embodiments, the message confirming identification of the ingested mediations is displayed on user interface 115 of mobile device 110. In other embodiments, the message may be transmitted to another smart device or computing device (not shown) and included in a medication history log.

Having completed generation of a notice or message associated with determining the identification of medications during the ingestion event of the user, identification program 300 ends.

Figure 4:
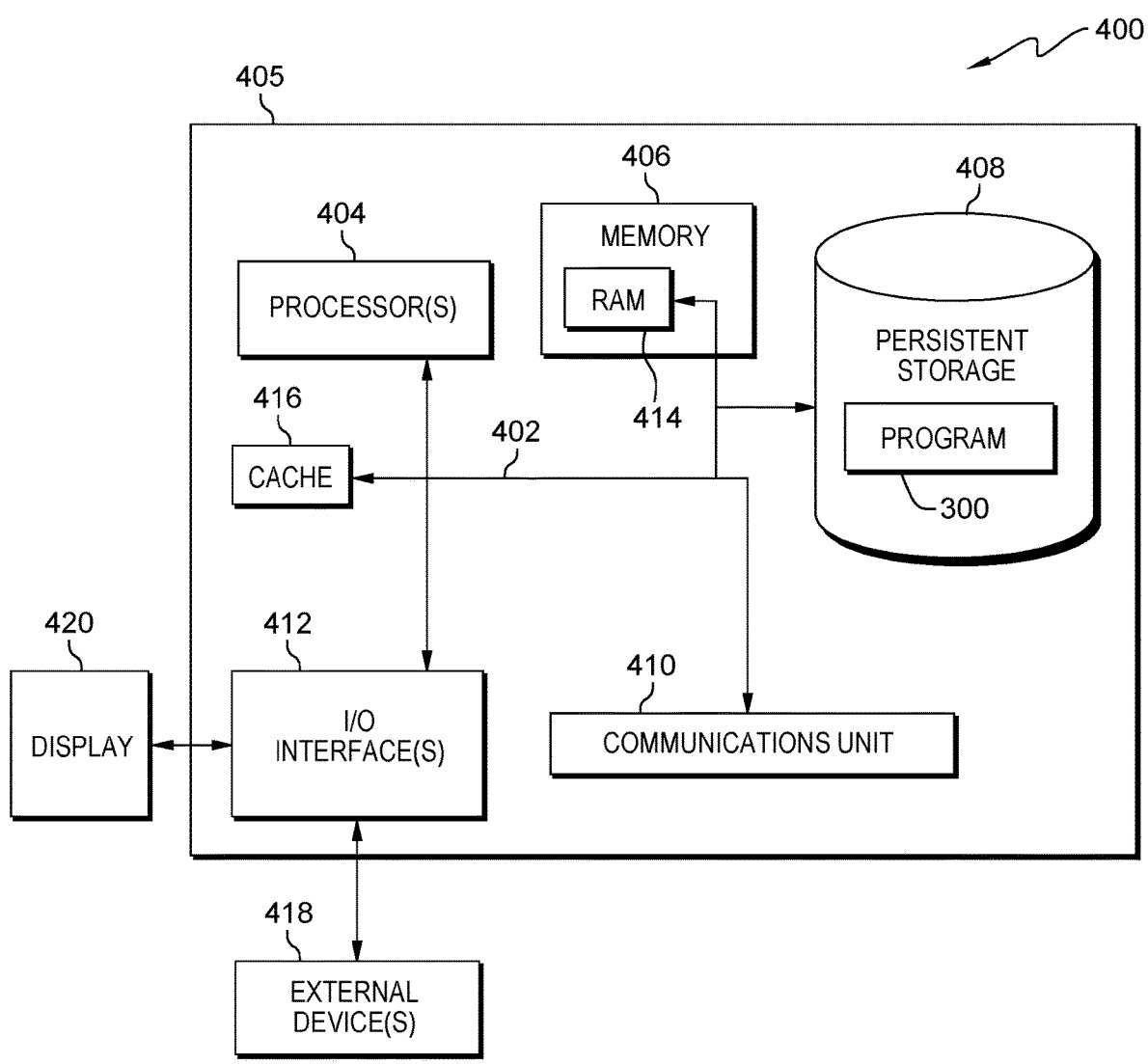
FIG. 4 depicts a block diagram of components of a computing system, including a computing device capable of operationally performing the identification program of FIG. 3, in accordance with an embodiment of the present invention.

FIG. 4 depicts a block diagram of components of computing system 400, including a computing device 405 capable of operationally performing identification program 300 of FIG. 3, in accordance with an embodiment of the present invention.

Computing device 405 includes components and functional capability similar to mobile device 110 (FIG. 1), in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Computing device 405 includes communications fabric 402, which provides communications between computer processor(s) 404, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406, cache memory 416, and persistent storage 408 are computer readable storage media. In this embodiment, memory 406 includes random access memory (RAM) 414. In general, memory 406 can include any suitable volatile or non-volatile computer readable storage media.

In one embodiment, identification program 300 is stored in persistent storage 408 for execution by one or more of the respective computer processors 404 via one or more memories of memory 406. In this embodiment, persistent storage 408 includes a magnetic hard disk drive. Alternatively, or in addition to a magnetic hard disk drive, persistent storage 408 can include a solid-state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices, including resources of distributed data processing environment 100. In these examples, communications unit 410 includes one or more network interface cards. Communications unit 410 may provide communications through the use of either or both physical and wireless communications links. Identification program 300 may be downloaded to persistent storage 408 through communications unit 410.

I/O interface(s) 412 allows for input and output of data with other devices that may be connected to computing system 400. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., identification program 300, can be stored on such portable computer readable storage media and can be loaded onto persistent storage 408 via I/O interface(s) 412. I/O interface(s) 412 also connect to a display 420.

Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for non-invasive detection of ingested medication, the method comprising:
    receiving, by one or more computer processors, images of medications designated for a user pre-captured prior to ingestion of the medications by the user;
    capturing, by one or more computer processors, an ultrasound image during an ingestion by the user;
    determining, by one or more computer processors, whether contents of the ingestion by the user includes one or more of the medications designated for the user by comparing the images of medication pre-captured prior to ingestion by the user to the ultrasound image captured during the ingestion by the user; and
    responsive to determining the contents of the ingestion by the user includes one or more of the medications designated for the user, generating, by one or more computer processors, a confirmation that includes identification of the detected medications ingested by the user.

2. The computer-implemented method of claim 1, wherein receiving images of medications designated for a user prior to ingestion of the medications by the user includes one or both of: ultrasound images and digitized camera images of the medications designated for the user.

3. The computer-implemented method of claim 1, wherein the images of medications captured include individual medications and combinations of groups of the medications.

4. The computer-implemented method of claim 1, further comprising:
    capturing, by the one or more computer processors, a second ultrasound image during ingestion of a liquid;
    generating, by the one or more computer processors, baseline image data based on the second ultrasound image captured during ingestion of the liquid; and
    modifying, by one or more computer processors, data of the ultrasound image captured during ingestion of the medications by the user to remove the baseline image data.

5. The computer-implemented method of claim 1, wherein the ultrasound device is included in a patch removably adhered to an area of a throat of the user.

6. The computer-implemented method of claim 1, wherein the received images of medication designated for the user prior to ingestion include ultrasound images captured through a membrane simulating throat tissue of the user.

7. The computer-implemented method of claim 1, further comprising:
    training, by the one or more computer processors, an analytical engine based on supervised machine learning using identified ultrasound images of ingested medications and images of identified medications captured prior to ingestion; and
    determining, by one or more computer processors, an identity of the medications included in the ingestion of the medications by the user, based on the images of medications designated for the user pre-captured prior to ingestion of the medications by the user.

8. A computer program product for non-invasive detection of ingested medication, the computer program product comprising:

one or more computer readable storage media and program instructions stored on the one or more computer readable storage media, the program instructions comprising:

program instructions to receive images of medications designated for a user pre-captured prior to ingestion of the medications by the user;

program instructions to capture an ultrasound image during an ingestion by the user;

program instructions to determine whether contents of the ingestion by the user includes one or more of the medications designated for the user by comparing the images of medication pre-captured prior to ingestion by the user to the ultrasound image captured during the ingestion by the user; and responsive to determining the contents of the ingestion by the user includes one or more of the medications designated for the user, program instructions to generate a confirmation that includes identification of the detected medications ingested by the user.

9. The computer program product of claim 8, wherein program instructions to receive images of medications designated for a user prior to ingestion of the medications by the user includes one or both of: ultrasound images and digitized camera images of the medications designated for the user.

10. The computer program product of claim 8, wherein the images of medications captured include individual medications and combinations of groups of the medications.

11. The computer program product of claim 8, further comprising:

program instructions to capture a second ultrasound image during ingestion of a liquid;

program instructions to generate baseline image data based on the second ultrasound image captured during ingestion of the liquid; and program instructions to modify data of the ultrasound image captured during ingestion of the medications by the user to remove the baseline image data.

12. The computer program product of claim 8, wherein the ultrasound device is included in a patch removably adhered to an area of a throat of the user.

13. The computer program product of claim 8, wherein the program instructions to receive images of medication designated for the user prior to ingestion include ultrasound images captured through a membrane that simulates throat tissue of the user.

14. The computer program product of claim 8, further comprising:

program instructions to train an analytical engine based on supervised machine learning using identified ultrasound images of ingested medications and images of identified medications captured prior to ingestion; and program instructions to determine an identity of the medications included in the ingestion of the medications by the user, based on the images of medications designated for the user pre-captured prior to ingestion of the medications by the user.

15. A computer system for non-invasive detection of ingested medication, the computer system comprising:

one or more computer processors;

one or more computer readable storage media; and program instructions stored on the one or more computer readable storage media, the program instructions comprising:

one or more computer readable storage media and program instructions stored on the one or more computer readable storage media, the program instructions comprising:

program instructions to receive images of medications designated for a user pre-captured prior to ingestion of the medications by the user;

program instructions to capture an ultrasound image during an ingestion by the user;

program instructions to determine whether contents of the ingestion by the user includes one or more of the medications designated for the user by comparing the images of medication pre-captured prior to ingestion by the user to the ultrasound image captured during the ingestion by the user; and responsive to determining the contents of the ingestion by the user includes one or more of the medications designated for the user, program instructions to generate a confirmation that includes identification of the detected medications ingested by the user.

16. The computer system of claim 15, wherein program instructions to receive images of medications designated for a user prior to ingestion of the medications by the user includes one or both of: ultrasound images and digitized camera images of the medications designated for the user.

17. The computer system of claim 15, further comprising:

program instructions to capture a second ultrasound image during ingestion of a liquid;

program instructions to generate baseline image data based on the second ultrasound image captured during ingestion of the liquid; and program instructions to modify data of the ultrasound image captured during ingestion of the medications by the user to remove the baseline image data.

18. The computer system of claim 15, wherein the ultrasound device is included in a patch removably adhered to an area of a throat of the user.

19. The computer system of claim 15, wherein the program instructions to receive images of medication designated for the user prior to ingestion include ultrasound images captured through a membrane that simulates throat tissue of the user.

20. The computer system of claim 15, further comprising:

program instructions to train an analytical engine based on supervised machine learning using identified ultrasound images of ingested medications and images of identified medications captured prior to ingestion; and program instructions to determine an identity of the medications included in the ingestion of the medications by the user, based on the images of medications designated for the user pre-captured prior to ingestion of the medications by the user.

* * * * *